US 7,993,521 B2

(12) United States Patent
Eichler et al.

(10) Patent No.: US 7,993,521 B2
(45) Date of Patent: Aug. 9, 2011

(54) PLANT AND METHOD FOR GENERATING BIOGAS FROM BIOLOGICALLY DEGRADABLE MATERIAL CONTAINING LIQUID AND SOLID COMPONENTS, IN PARTICULAR WASTE PRODUCTS, AND A BIOGAS GENERATION CONTAINER FOR USE IN THE PLANT

(76) Inventors: Dietrich Eichler, Grosskarolinenfeld (DE); Friedrich Weigand, Soest (DE); Matthias Rabener, Oelde (DE)

( * ) Notice: Subject to any disclaimer, the term of this patent is extended or adjusted under 35 U.S.C. 154(b) by 9 days.

(21) Appl. No.: 11/919,451

(22) PCT Filed: Dec. 12, 2006
(Under 37 CFR 1.47)

(86) PCT No.: PCT/EP2006/011948
§ 371 (c)(1),
(2), (4) Date: Mar. 30, 2009

(87) PCT Pub. No.: WO2007/068446
PCT Pub. Date: Jun. 21, 2007

(65) Prior Publication Data
US 2009/0218279 A1    Sep. 3, 2009

(30) Foreign Application Priority Data

Dec. 14, 2005  (DE) .................. 10 2005 059 723
Feb. 9, 2006   (DE) .................. 10 2006 005 859

(51) Int. Cl.
*C02F 11/04* (2006.01)
*C02F 3/28* (2006.01)
(52) U.S. Cl. .................. 210/603; 210/608; 210/259
(58) Field of Classification Search ................ 210/603, 210/608, 252, 259; 435/262, 262.5; 71/10
See application file for complete search history.

(56) References Cited

U.S. PATENT DOCUMENTS
4,948,509 A    8/1990  Stack
(Continued)

FOREIGN PATENT DOCUMENTS
DE    31 06 422 A1    9/1982
DE    37 33 583 A1    4/1989
(Continued)

OTHER PUBLICATIONS
International Search Report dated Apr. 10, 2007.

*Primary Examiner* — Fred Prince
(74) *Attorney, Agent, or Firm* — Edwards Angell Palmer & Dodge LLP (57) ABSTRACT

A plant for generating biogas from organic biodegradable material containing liquid and solid components, such as waste products, in particular liquid manure from agricultural enterprises, comprises a biogas generation container (9) having a feed for the degradable material and a biogas collection zone (6) having a biogas outlet, and a flotation separation unit having a microbubble generation unit (15) for separating off the solid components from the liquid components of the degradable material. The flotation separation unit comprises a chamber region (14) which is delimited in the interior of the biogas generation container and essentially active in the direction of gravity and having a closed bottom and an open upper end arranged below the liquid level of the biogas generation container. Clarified liquid form the chamber region and a gas, in particular the biogas from the biogas collection region, can be fed to the microbubble generation unit for charging the liquid with gas. The outlet of the microbubble generation unit is connected to an inlet (18) of the chamber region in order to recycle microbubble-forming clarified liquid to the chamber region. Near the bottom of the chamber region, an outlet (116) for clarified liquid from the chamber region is provided. The flotation separation takes place in the chamber region in countercurrent flow to the ascending microbubbles.

14 Claims, 5 Drawing Sheets

U.S. PATENT DOCUMENTS

| | | | |
|---|---|---|---|
| 5,015,384 A | 5/1991 | Burke | |
| 5,185,079 A * | 2/1993 | Dague | 210/603 |
| 5,670,047 A | 9/1997 | Burke | |
| 6,132,601 A * | 10/2000 | March et al. | 210/150 |
| 2003/0121851 A1 * | 7/2003 | Lee, Jr. | 210/603 |
| 2004/0031742 A1 * | 2/2004 | Arnaud | 210/259 |
| 2005/0098497 A1 * | 5/2005 | Khudenko | 210/620 |

FOREIGN PATENT DOCUMENTS

| | | |
|---|---|---|
| DE | 102 51 923 A1 | 5/2004 |
| DE | 602 01 182 T2 | 10/2005 |
| EP | 0 367 037 B1 | 12/1993 |
| JP | 60 220194 A | 11/1985 |
| JP | 2002 001310 A | 1/2002 |
| WO | WO 98/19971 | 5/1998 |

* cited by examiner

PLANT AND METHOD FOR GENERATING BIOGAS FROM BIOLOGICALLY DEGRADABLE MATERIAL CONTAINING LIQUID AND SOLID COMPONENTS, IN PARTICULAR WASTE PRODUCTS, AND A BIOGAS GENERATION CONTAINER FOR USE IN THE PLANT

The invention relates to a plant and a method for generating biogas from organic biologically degradable material containing liquid and solid components, in particular waste products such as liquid manure from agricultural facilities, and further to a biogas generation container or tank for use in the plant.

The invention relates in particular to a process of concentrating anaerobic biomass in fermenters for the purpose of generating biogas.

A conventional plant (U.S. Pat. No. 5,015,384 A) comprises a biogas generating tank from the upper part thereof the extracted biogas can be removed, and a floatation-type separating device located outside the tank. Liquid biomass derived from the tank can be introduced into the device together with a gas for forming micro-bubbles in order to separate solids from the biomass. These are re-introduced into the tank, whereas the purified liquid can be fed out for further use. The flotation-type separation operation thus takes place outside the biogas generating tank in a separate flotation separator.

An object of the invention is to provide a biogas generating plant adapted to be designed in compact manner, and a corresponding method having increased effectiveness in regard to the yield of biogas per unit time whereby lower operating and capital costs can be achieved.

Reference is made to claims 1 and 8 for achieving this object.

A feature of the invention is a flotation-type separation operation into liquid and solid constituents within the biogas generating tank by means of a chamber zone confined therein. Clarified liquid is produced in the chamber zone and can be withdrawn from the lower part thereof. At the same time, there is a continuous exchange of separated solid biomass from the chamber zone for mixing with the waste products present in the tank and of waste products into the chamber zone without the need to use separate feed and discharge line systems for this purpose. A continuous build-up in the concentration of the anaerobic biomass for the purposes of generating biogas is thereby obtained, whereby the effectiveness of the plant is substantially increased. In accordance with an embodiment of the invention, the production of micro-bubbles in the chamber zone can be effected in that a branched partial stream of the clarified liquid is supplied from the chamber zone to a gasification means and gasified liquid is then fed back into the chamber zone where the gas is set free in the form of micro-bubbles due to expansion effects. In accordance with another embodiment, a gas can be introduced into a porous substrate in the chamber zone, whereby gas bubbling out from the substrate in the form of micro-bubbles. The micro-bubbles produced should be as fine as possible in order to capture a large amount of the solid biomass by the effects of surface tension and force it upwards in the chamber zone. The confined chamber zone ends at an adequate distance below the level of the liquid in the biogas tank. Consequently, the waste products supplied to the chamber zone flow through the confined zone from the top in a direction opposite to that of the ascending stream of micro-bubbles.

The biologically degradable material is preferably submitted to an additional mechanical separating stage for separating it into its liquid and solid constituents, preferably by means of a press screw separator, before or after being introduced into the biogas generating tank. In accordance with a further embodiment of the invention, the liquid constituents obtained from the mechanical separation stage can be sub-divided into different partial amounts and fed back into the chamber zone. A certain advantageous split into streams of liquid having different rates of flow and directed towards the bottom and the open end of the chamber zone in a direction opposite to that of the ascending stream of micro-bubbles is thereby obtained in the chamber zone, whereby the effectiveness of the plant can be raised still more. In accordance with a further aspect of the invention, a biogas generating tank is provided.

The invention is described in more detail hereinafter with reference to embodiments thereof and the drawing. In the drawings.

Although the invention is described hereinafter and is illustrated in the drawing in connection with the generation of biogas from liquid manure resulting from agricultural facilities, it is to be understood that the protection of the invention is not to be considered as being restricted to this application. Rathermore, it can also be advantageously used for obtaining biogas from materials and wastes from other sources, and in particular communal or industrial facilities.

Figure 1:
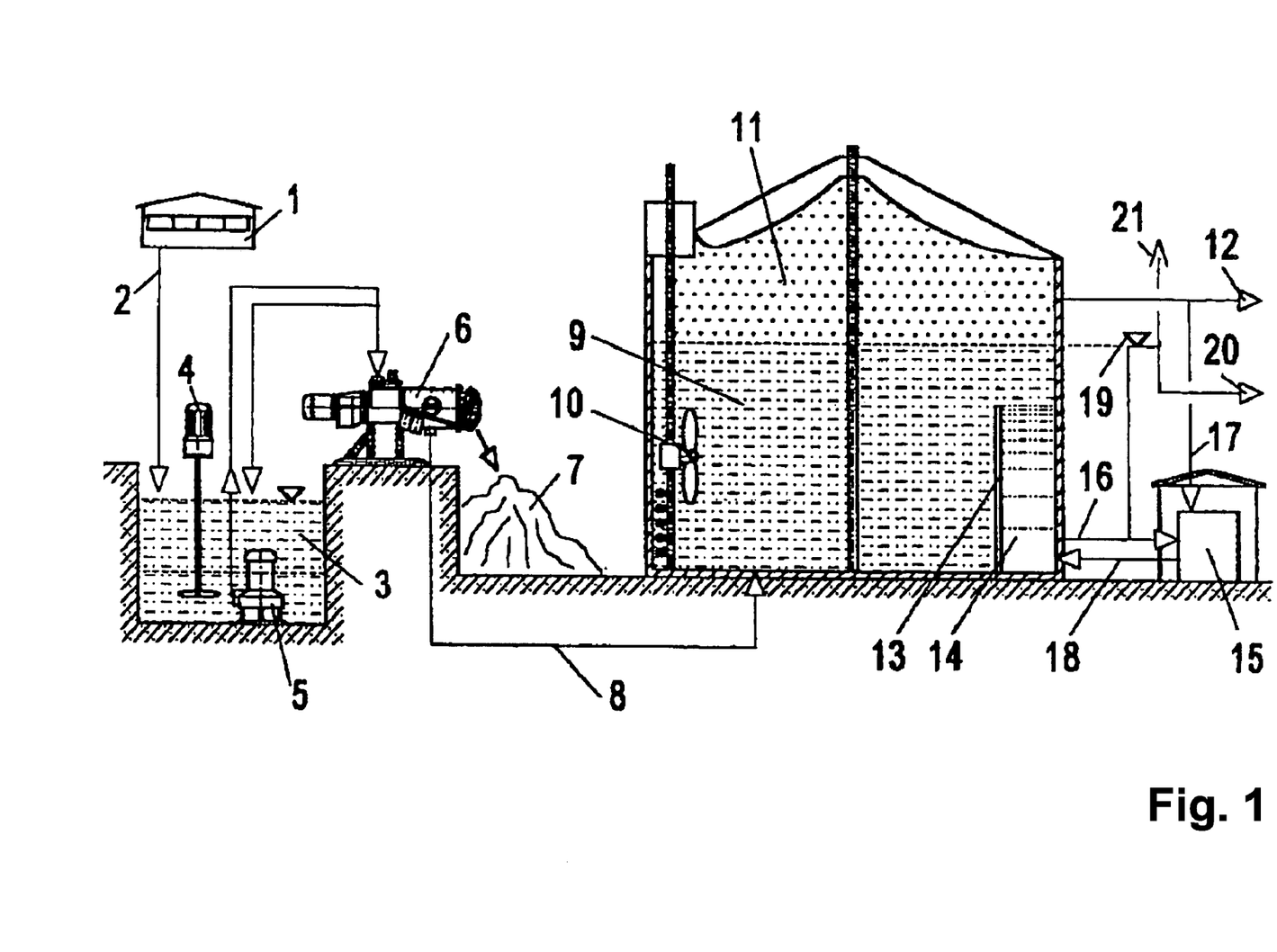
FIG. 1 is a schematic, partially sectional view of a biogas plant in accordance with a first embodiment of the invention, integrated into a plant for separating liquid manure obtained from agricultural facilities into liquid and solid constituents.

In the first embodiment of the invention shown in FIG. 1, the liquid manure containing liquid and solid constituents and emanating from a stable area 1 is passed through a line 2 into a collecting tank 3; it can be homogenized therein by means of an agitator 4. A pump 5 is provided in order to supply the homogenized liquid manure from the collecting tank 3 to a solid/liquid separator 6. The solid/liquid separator 6 is preferably a press screw separator such as is described e.g. in EU-B-0367037 so that reference can be made thereto for further details. Other types of solid/liquid separators could likewise be employed if so desired.

The solid phase separated in the solid/liquid separator 6 can be formed into a pile, as indicated at 7, and can be spread over fields as a fertilizer, possibly in composted form, or it can be used as bedding in stables after being subjected to a suitable aerobic treatment.

The liquid phase of the liquid manure that has been freed to a large extent from the solid constituents is fed through a line 8 into a biogas generating tank or biogas fermenter 9 in a biogas plant constructed in accordance with the present invention. An agitator 10 is provided in the tank 9 in order to constantly mix and stir the liquid contained therein which is indicated by dash-dotted lines in the drawing.

In place of or in addition to an agitator 10, provision could also be made for a circulating pump system (not shown)

wherein a circulating pump sucks the liquid from the tank and then feeds it back in tangentially.

The formation of the biogas is effected by fermenting the biomass in the presence of anaerobic bacteria as is in principle known to the skilled person so that a more detailed explanation of this process is unnecessary.

Although this is not illustrated in the drawing, provision could also be made for a further separation step for separating out fine solid materials in the form of e.g. fine sand-like constituents that might still remain in the liquid output of the solid/liquid separator 6. Preferably, this separation operation can be effected by means of a centrifugal separator integrated into the line 8. The additional separation operation ensures that muddy deposits consisting of fine particles that are not biologically degradable will not be formed in the biogas generating tank 9.

As is indicated by dotted lines in the drawing, the resulting biogas collects in the upper portion 11 of the tank 9 which serves as a biogas reservoir and is covered by a foil or the like. From there, the biogas can be fed off through a line 12 for further use, e.g. for generating electricity by means of a micro gas turbine.

Figure 4:
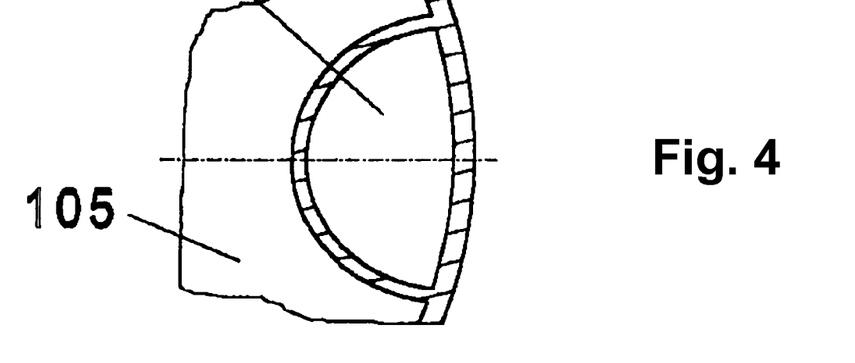
FIG. 4 is a cross sectional plan view of the confined chamber zone of the biogas tank shown in FIG. 3.

In accordance with the invention, in the interior of the tank 9 there is provided a partition 13 projecting upwardly from the bottom of the tank and creating an upwardly open confined zone 14 in the tank 9, c.f. also FIG. 4. The partition 13 ends at a suitable distance of e.g. about 0.5 to 1.0 m, below the fluid level in the tank 9, as is indicated by dashed lines in the drawing.

A further separation of liquid and any solid biomass still present therein takes place in the confined zone 14 in accord with a flotation-type separation principle. To this end, purified liquid is fed off outwardly through a line 16 near the bottom of the confined zone 14 and supplied to a means 15 for generating micro-bubbles. Such micro-bubble generating means are known to the skilled person. They serve to create micro gas bubbles suitable for a flotation-type separation process by means of charging or loading liquid with gas at high pressure and then causing the liquid to expand in flow-intensive manner in a field of cavitation. In the plant according to the invention, the gas is a portion of the biogas which is branched off from the line 12 and introduced through the line 17 into the micro-bubble generating means 15. In particular, biogas can be sucked out by restricting the flow of the stream of liquid before a centrifugal pump (not shown) and it is then introduced under pressure into the purified liquid so as to be dissolved therein. Dissolved components of the gas are then wrenched from the liquid in the cavitation field by means of a flow-intensive expansion process. Micro-bubbles in a μm-range are thereby formed. The construction of one type of micro-bubble means is described e.g. in DE 3733583 A.

The clarified liquid charged with gas is fed back through a line 18 into the confined zone 14 close to the bottom thereof. The gas bubbles bubbling out of the liquid rise upwardly in the confined zone 14, whereas the liquid biomass introduced into the tank 9 through the line 8 flows into the confined zone 14 from the top in a direction opposed to that of the stream of ascending micro-bubbles. Whilst floating upwardly, the micro-bubbles carry any particles in the liquid biomass upwardly therewith so that clarified and, to a large extent, now odorless liquid remains near the bottom of the confined zone 14. Due to the effects of surface tension, very fine particles in the biomass also attach themselves to the micro-bubbles and are carried upwardly therewith.

The clarified liquid can be fed out externally through a line 20 branching off from the line 16. A venting means 21 can be provided in order to ensure that there is always a constant suction-free flow in the line 20. The reference 19 indicates the overflow height which is defined by the line 20; this height determining the maximum level for the liquid biomass in the tank 9.

The agitator 10 keeps the liquid biomass in motion throughout the entire tank 9 and at the same time guides the solid biomass that is ascending as a result of the flotation process away from the confined zone 14 and mixes it with the remaining contents of the tank 9.

For the purposes of assisting the mixing of the separated solid biomass with the remaining contents of the tank 9, the suction side of the agitator 10 can be provided with a guide tube (not shown) led from a possibly forming floating layer of biomass near the confined zone 14 to the rear of the agitator 10.

Figure 2:
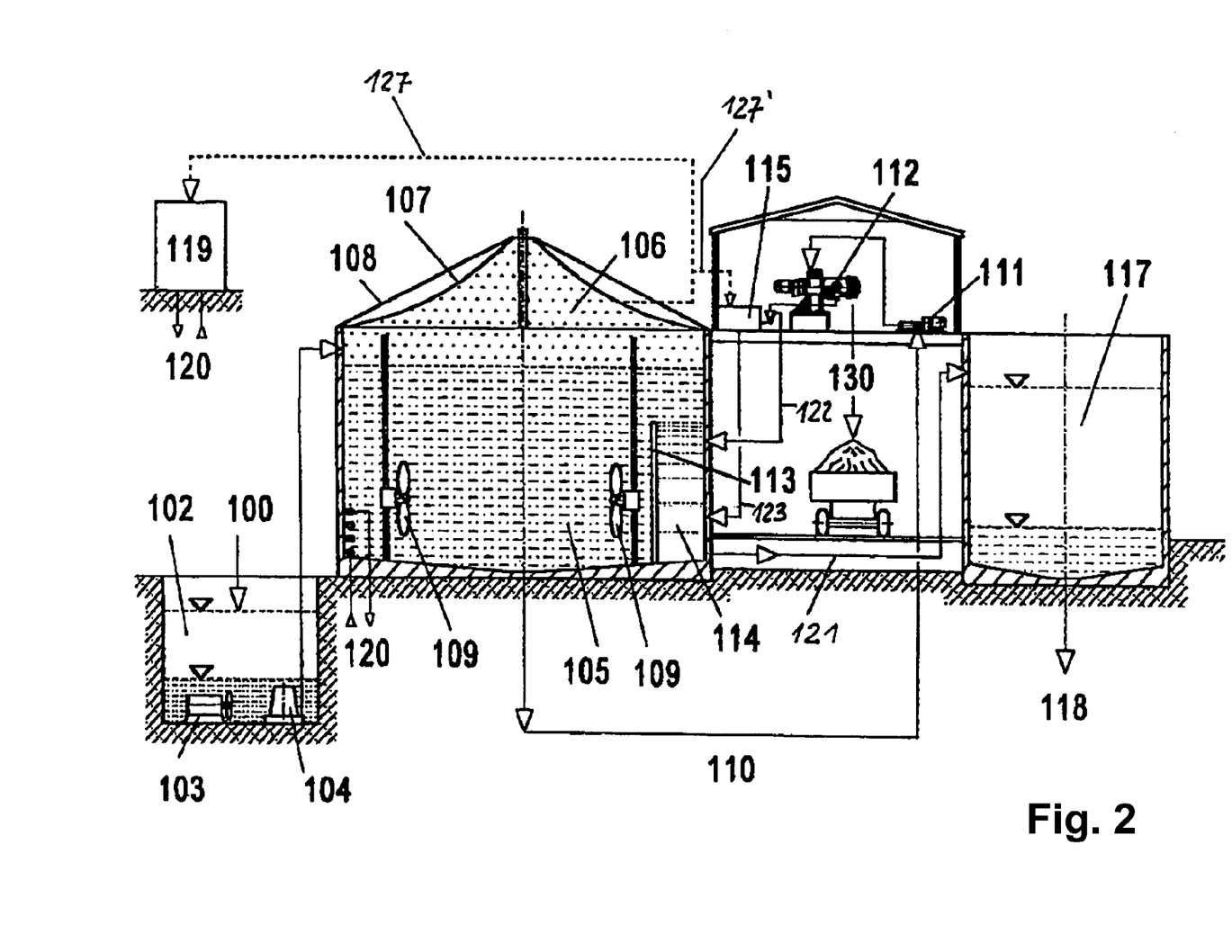
FIG. 2 is a view similar to FIG. 1 of a biogas plant and its surroundings in accordance with a second embodiment of the invention.
Figure 3:
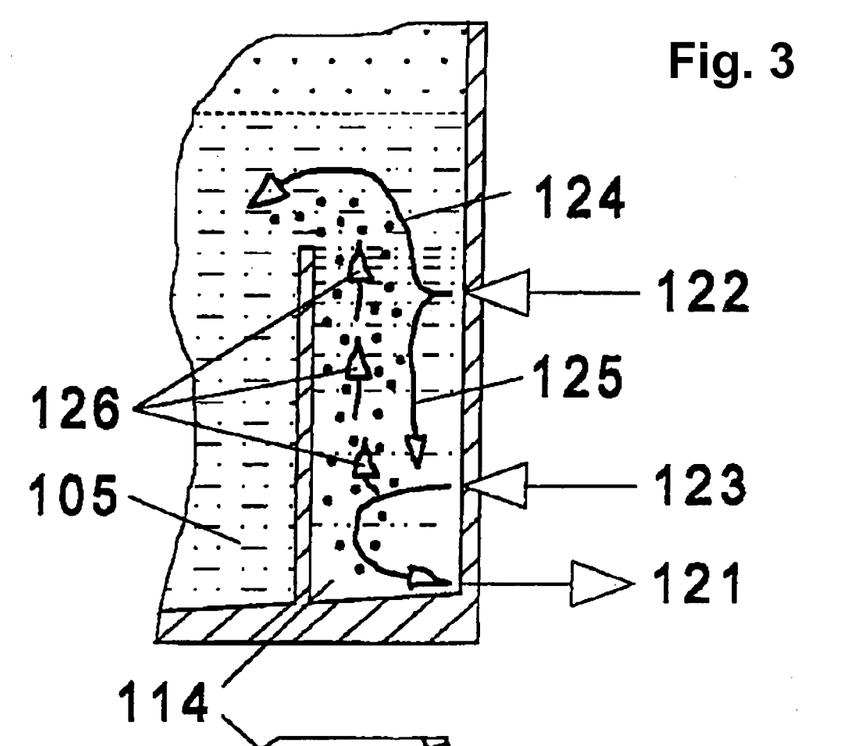
FIG. 3 is an enlarged fragmentary view of a confined chamber zone of a biogas tank in the biogas plant of FIG. 2.

A second embodiment of the invention is shown in FIGS. 2 to 4.

In this embodiment in like manner to the previously described first embodiment, liquid manure 100 incorporating liquid and solid constituents and emanating from a stable area (not shown) is fed at a certain rate into a collecting tank 102 and can be homogenized therein by means of an agitator 103. A pump 104 supplies the liquid from the collecting tank 102 to a biogas tank 105. The biogas 106 formed therein collects under a collecting foil 107 which can be strengthened by an e.g. PVC coated polyester cloth 108. The biogas can be fed off from there for further use.

A pair of agitators 109 at diametrically opposite positions in the biogas tank 105 can be provided in order to constantly mix the contents of the tank.

As was the case in the first embodiment of the invention, a partition 113 projecting upwardly from the bottom of the tank is provided in the interior of the tank 105, said partition creating an upwardly open confined zone 114 within the tank 105, see also FIG. 4. The partition 113 ends at a suitable distance of e.g. about 0.5 to 1.0 m below the fluid level in the tank 105 which is indicated by dashed lines in the drawing.

Liquid manure can be withdrawn from the bottom of the biogas tank 105 through an extraction pipe 110 to a location outside the confined zone 114 by means of a pump 111 and supplied to a solid/liquid separator 112. The solid/liquid separator 112 is preferably a press screw separator in like manner to the first embodiment.

In accordance with the invention, the amount per unit time at which liquid manure is withdrawn from the biogas tank 105 is approximately 10 to 20% greater than the throughput through the plant.

The solid constituents in the liquid manure are separated in the separator 112. The separated solid can be piled up, as is indicated by 130, for further use e.g. for transportation by means of a trailer.

A larger part of the entire amount of liquid running out of the separator 112 is supplied through a line 122 to the confined zone 114 of the biogas tank 105 at a suitable point near the open upper end thereof, preferably e.g. within the upper third thereof. As in the previously described first embodiment of the invention, a centrifugal separator or another suitable separation means for separating fine, e.g. sandy non bacterially degradable constituents in the liquid can be provided in the line 122.

A smaller partial stream of the quantity of liquid running from the separator 112 is supplied to a means 115 for forming micro-bubbles and leaves the means in the form of a liquid packed with micro-bubbles which is fed through a line 123 into the confined zone 114 at a suitable position close to its bottom, preferably within the lower third thereof.

The micro-bubble means 115 may be of similar construction to that of the first embodiment of the invention. Again, a portion of the resultant biogas is preferably used as the gas, as is indicated in FIG. 2 by the branch line 127' shown in dashed-lines.

The liquid now reduced of its solid components can be fed out from the confined zone 114 of the biogas plant through a drain line 121 provided near the bottom of the confined zone 114 and collected in a temporary storage facility 117 for further use. For example, the liquid collected in the temporary storage facility 117 can be made available as a liquid fertilizer for agricultural purposes through a run-off 118.

The biogas that has been produced can be supplied through a line 127 to a block heating station 119 for further use, e.g. for generating electricity or heat. The resultant heat can be used for heating up the contents of the biogas tank 105 by means of a heat exchanger provided therein, as is indicated by 120, for the purposes of assisting the biological decomposition process.

The flow patterns resulting from the aforementioned supply of liquid to the confined zone 114 are explained hereinafter with reference to FIG. 3.

The smaller partial stream enters the confined zone 114 through the line 122, whilst the main stream is introduced through the line 123 so that, in toto, the sum of both these partial amounts arrives in the confined zone 114. A certain quantity of liquid that has been reduced of its solid components is withdrawn through the line 121 arranged near the bottom of the separated zone 114. Hereby, the liquid originating from the line 122 divides into a partial stream 124 having a smaller rate of flow which flows back into the biogas tank 105, whilst a partial stream 125 having a greater rate of flow flows to the bottom of the confined zone 114 and is fed outwardly through the drain line 121.

The micro-bubbles 126 from the quantity of gasified liquid supplied through the line 123 float upwardly against the partial stream 125 due to their buoyancy and thereby unite with the solid biomass in the partial stream 125 by virtue of their surface tension, thereby solid biomass is returned to the biogas tank 105 together with the partial stream 124.

FIG. 4 shows the confined zone 114 in the form of a plan view. As can be perceived, the partition 113 extends in the shape of an arc from an attachment point on one side wall of the biogas tank 105 to a peripherally spaced attachment point so that the confined zone 114 can have a cross section which is substantially in the form of a segment of a circle. The invention is not however limited to such a configuration of the confined zone 114 and in consequence, it could also be formed in some other suitable manner.

EXAMPLE 1

10 m³/h of separated liquid reaches the solid/liquid separator 112. This is divided into a larger partial amount of 9 m³/h and a smaller partial amount of 1 m³/h. The larger partial amount is introduced through the line 122 into an upper third of the chamber zone 114, the smaller partial amount being introduced into the lower third through the line 123 after a gasification process. 8 m³/h of clarified liquid is withdrawn from the chamber zone through the line 121. The quantity per unit time of the upwardly directed stream of fluid 124 within the chamber zone amounts to 2 m³/h, and that of the downwardly directed stream 125 amounts to 7 m³/h. The downwardly directed stream 125 and the partial amount at 123 thus correspond in sum to the 8 m³/h of the withdrawn stream 121.

Figure 5:
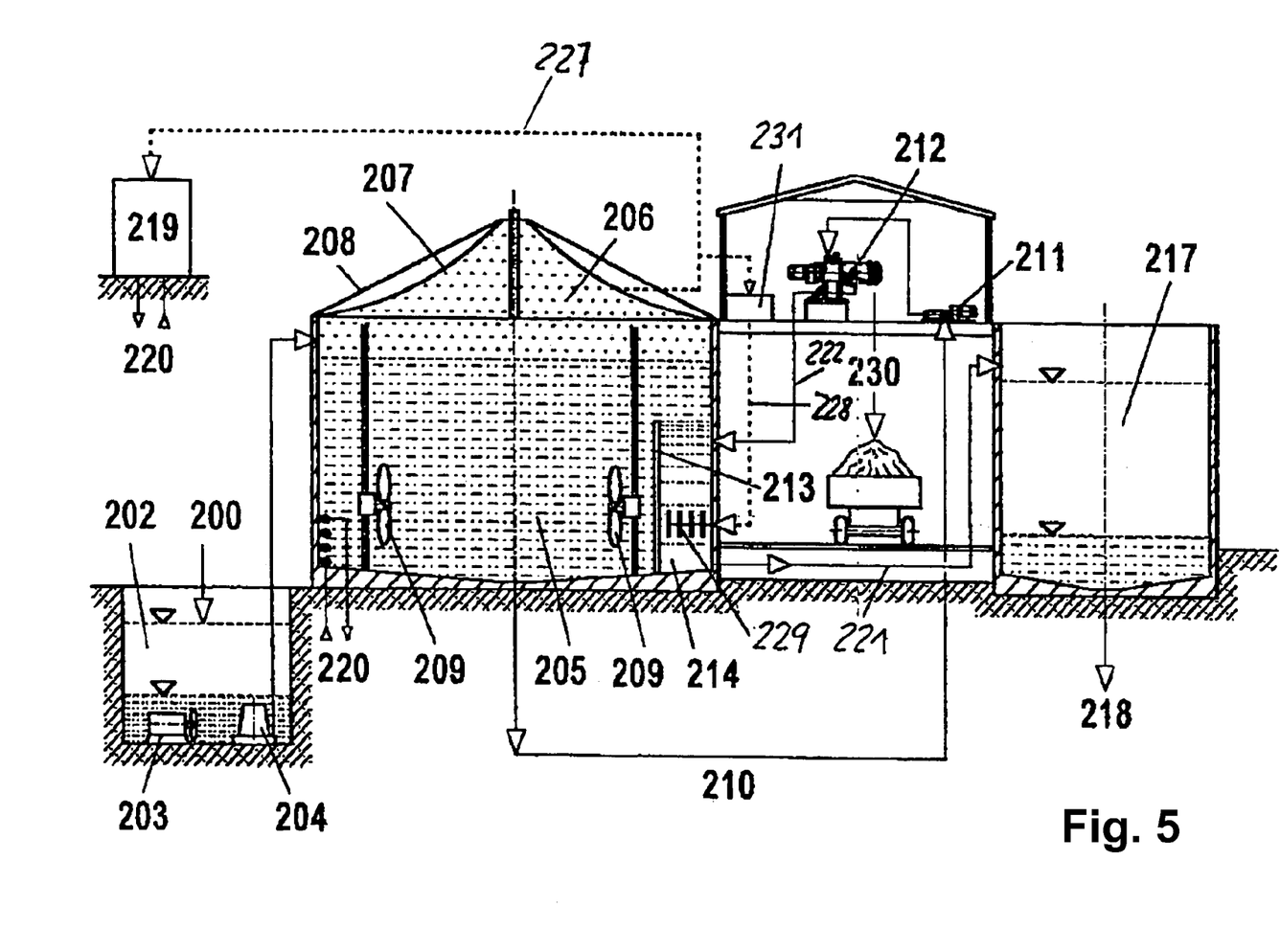
FIG. 5 is a view similar to FIG. 1 of a biogas plant in accordance with a third embodiment of the invention.
Figure 6:
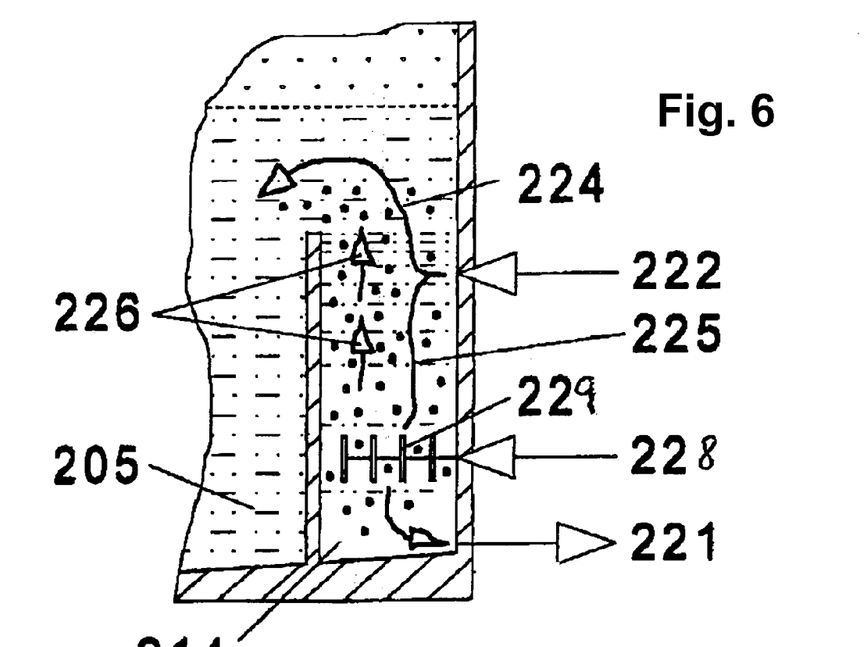
FIG. 6 is a sectional view similar to FIG. 4 of the confined chamber zone of the biogas tank shown in FIG. 5.
Figure 7:
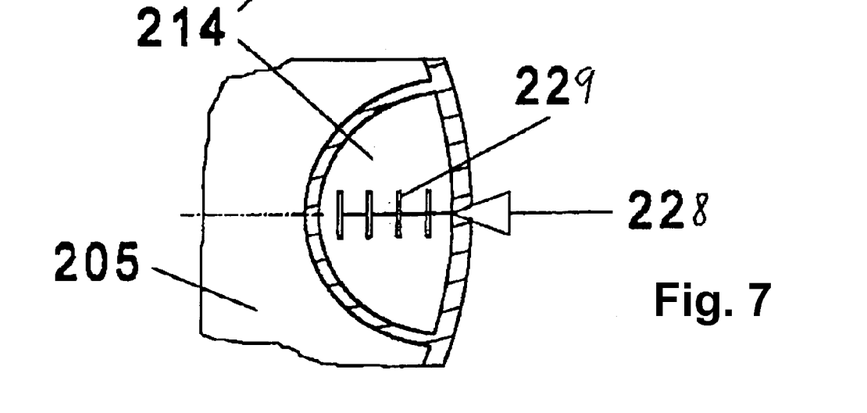
FIG. 7 is a cross sectional plan view of the confined chamber zone of the biogas tank shown in FIG. 5.

A third embodiment of the invention is shown in FIGS. 5 to 7. This distinguishes essentially from the second embodiment by virtue of a modified arrangement for forming the micro-bubbles in the confined chamber zone so that reference can be made to the description of the second embodiment in regard to the remaining components. Equivalent or similar components thus bear the same reference symbols, but the first digit of the number is changed to "2-".

In contrast to the previously described embodiments, the micro-bubbles are not formed by means of a micro-bubble means located externally of the biogas tank, but rather, they are formed in the interior thereof by means of a disk-shaped substrate 229 made of micro-pored ceramic provided at a position in the confined chamber zone 214 close to the bottom thereof. A pressurised gas can be introduced into the disk-shaped substrate 229 through a line 228, whereby the gas can bubble out of the micro-pored ceramic substrate 229 in the form of micro-bubbles. A suitable micro-pored ceramic substrate material can be obtained under the trade name "Kerafol" from Keramische Folien GmbH, Stegenthumbach 4-6, D-92676 Eschenbach/Germany. Again, the gas is preferably the biogas which is extracted from the biogas tank 205 and is subjected to a suitable pressure by means of a compressor 231 integrated in the line 228 before it enters the micro-pored ceramic substrate 229.

EXAMPLE 2

10 m³/h of the separated liquid reaches the solid/liquid separator 212. This is introduced through the line 222 into an upper third of the chamber zone 214. 8 m³/h of clarified liquid is withdrawn from the chamber zone through the line 221. Biogas is fed into the micro-pored ceramic substrate 229 at a pressure of 2.2 bar through the line 228. The amount per unit time of the upwardly directed stream of fluid 224 within the chamber zone amounts to 2 m³/h and that of the downwardly directed stream 125 amounts to 8 m³/h.

Although gasification in the micro-bubble generating means by using the derived biogas was described hereinabove as being advantageous, it is to be understood that, if so desired, suitable foreign gases from a source of foreign gas can be used instead.

The invention claimed is:

1. A plant for generating biogas from organic biologically degradable material containing liquid and solid constituents, such as waste products, in particular liquid manure from agricultural facilities, comprising a biogas generating tank having an inlet for the biologically degradable material and a biogas collecting zone, said biogas collecting zone having a biogas outlet, and a flotation-type separating device including a micro-bubble generating means for separating the solid from the liquid constituents of the biologically degradable material, said flotation-type separating device comprising a chamber zone confined in the interior of the biogas generating tank, said chamber zone being effective substantially in the direction of the force of gravity and having a closed bottom and an open upper end located below the maximum level of the liquid in the biogas generating tank, wherein a gas, in particular biogas from the biogas collecting zone is adapted to be supplied to the micro-bubble generating means for forming micro-bubbles in said chamber zone, wherein the micro-bubble generating means is disposed outside the biogas generating tank, whereby clarified liquid from the chamber zone and gas for loading the clarified liquid with gas are supplied to the micro-bubble generating means, whilst an outlet of the micro-bubble generating means for the gas-loaded clarified liquid is connected to an inlet of the chamber zone, and wherein the inlet for the gas-loaded clarified liquid is provided near the bottom of the confined chamber zone.

2. The plant according to claim 1, wherein the micro-bubble generating means comprises a substrate material made of micro-pored ceramic and disposed within the chamber zone, whereby pressurised gas being adapted to be fed into said substrate.

3. The plant according to claim 1, further comprising agitator means in the interior of the biogas generating tank for mixing the contents of the tank.

4. The plant according to claim 3, wherein the agitator means comprises a guide tube for sucking off a floating layer of biomass formed near an open upper end of the chamber zone and feeding it towards behind the agitator means.

5. The plant according to claim 1, further comprising a solid/liquid separating means connected upstream of the biogas generating tank for separating solid constituents from the biologically degradable material before the introduction thereof into the biogas generating tank.

6. The plant according to claim 5, wherein the solid/liquid separating means comprises a press screw separator.

7. The plant according to claim 1, further comprising a solid/liquid separating means with an inlet thereof connected to a bottom outlet of the biogas generating tank, whilst a liquid outlet of the solid/liquid separating means is connected to an inlet of the chamber zone near the open end thereof, while an outlet for the clarified liquid is provided near the bottom of the chamber zone.

8. A biogas generating tank for use in a plant in accordance with claim 1, comprising:
  an inlet for biologically degradable material containing liquid and solid constituents, such as waste products, in particular liquid manure from agricultural facilities;
  a chamber zone confined within the interior of the biogas generating tank, said chamber zone being effective substantially in the direction of the force of gravity and having a closed bottom and an open upper end,
  said biogas generating tank is adapted to be filled to a maximum level above the open upper end of the chamber zone;
  at least one inlet near the bottom of the chamber zone for feeding a micro-bubble forming liquid into the chamber zone; and
  an outlet for a clarified liquid near the bottom of the chamber zone.

9. The biogas generating tank for use in a plant in accordance with claim 1, comprising:
  an inlet for biologically degradable material containing liquid and solid constituents, such as waste products, in particular liquid manure from agricultural facilities;
  a chamber zone confined within the interior of the biogas generating tank, said chamber zone being effective substantially in the direction of the force of gravity and having a closed bottom and an open upper end;
  said biogas generating tank is adapted to be filled to a maximum level above the open upper end of the chamber zone;
  a substrate material disposed near the bottom of the chamber zone and made of micro-pored ceramic material;
  an inlet for a compressed gas into said substrate material; and
  an outlet for clarified liquid from the chamber zone near the bottom thereof.

10. A method for generating biogas from organic biologically degradable material containing liquid and solid constituents, such as waste products, in particular liquid manure from agricultural facilities, comprising the steps of
  filling a biogas generating tank with the biologically degradable material up to a certain height level and substantially maintaining said height level,
  effecting a flotation-type separation operation for the separation of solid from liquid constituents of the biologically degradable material in a chamber zone confined in the interior of the biogas generating tank, said chamber zone being effective substantially in the direction of the force of gravity and having a closed bottom and an open upper end located below the maximum level of the liquid, whereby micro-bubbles are produced in the chamber zone,
  causing micro-bubbles formed in the chamber zone to float up in counter-flow to the biologically degradable material flowing into the chamber zone from the upper end thereof so that the solid constituents thereof are carried upwardly by the micro-bubbles, and
  extracting liquid substantially clarified from solid constituents near the bottom of the chamber zone, wherein the biologically degradable material is fed into the biogas generating tank and a quantity of organic material is removed from the biogas generating tank and submitted to a mechanical separation operation into solid and liquid constituents;
  and wherein:
  liquid obtained from the mechanical separation operation is sub-divided into first and second partial amounts, whereby the first partial amount is larger than the second partial amount,
  gas, in particular biogas from the biogas collecting area is introduced into the second partial amount in order to produce a gas-loaded liquid,
  said gas-loaded liquid is fed into the chamber zone close to the bottom thereof, whilst the first partial amount is fed into the chamber zone close to upper end thereof, and
  clarified liquid is removed from the chamber zone close to its bottom at a rate per unit time which is smaller than that of the first partial amount and larger than that of the second partial amount and also smaller than that of the sum of the first and second partial amounts so that the first partial amount is caused to divide into streams of liquid within the chamber zone which are directed towards the bottom and the open end thereof.

11. The method according to claim 10, wherein the biologically degradable material is subjected to a mechanical pre-separation operation into solid and liquid constituents before feeding into the biogas generating tank.

12. The method according to claim 10, wherein the introduction of the liquid obtained from the mechanical separation operation is effected in the upper third portion of the longitudinal extent of the chamber zone.

13. A method for generating biogas from organic biologically degradable material containing liquid and solid constituents, such as waste products, in particular liquid manure from agricultural facilities, comprising the steps of
  filling a biogas generating tank with the biologically degradable material up to a certain height level and substantially maintaining said height level,
  effecting a flotation-type separation operation for the separation of solid from liquid constituents of the biologically degradable material in a chamber zone confined in the interior of the biogas generating tank, said chamber zone being effective substantially in the direction of the force of gravity and having a closed bottom and an open upper end located below the maximum level of the liquid, whereby micro-bubbles are produced in the chamber zone, causing micro-bubbles formed in the chamber zone to float up in counter-flow to the biologically degradable material flowing into the chamber zone from the upper end thereof so that the solid constituents thereof are carried upwardly by the micro-bubbles, and extracting liquid substantially clarified from solid constituents near the bottom of the chamber zone, wherein the biologically degradable material is fed into the biogas generating tank and a quantity of organic material is removed from the biogas generating tank and submitted to a mechanical separation operation into solid and liquid constituents, and wherein:

liquid obtained from the mechanical separation operation is fed into the chamber zone close to the upper end thereof, the micro-bubbles are formed in the chamber zone close to bottom thereof, and clarified liquid is removed from the chamber zone close to the bottom at a rate per unit time which is smaller than that of the quantity of liquid supplied from the mechanical separation process so that the latter quantity is caused to divide into streams of liquid within the chamber zone which are directed towards the bottom and the open end thereof.

14. The method according to claim 13, wherein the introduction of the liquid obtained from the mechanical separation operation is effected in the upper third portion of the longitudinal extent of the chamber zone.

\* \* \* \* \*